(12) United States Patent
Larsen et al.

(10) Patent No.: US 8,142,758 B2
(45) Date of Patent: Mar. 27, 2012

(54) ALPHA-EMITTING HYDROXYAPATITE PARTICLES

(75) Inventors: Roy H. Larsen, Olso (NO); Gro Salberg, Oslo (NO)

(73) Assignee: Algeta AS, Oslo (NO)

( * ) Notice: Subject to any disclaimer, the term of this patent is extended or adjusted under 35 U.S.C. 154(b) by 922 days.

(21) Appl. No.: 10/588,839

(22) PCT Filed: Feb. 18, 2005

(86) PCT No.: PCT/GB2005/000616
§ 371 (c)(1),
(2), (4) Date: Apr. 17, 2008

(87) PCT Pub. No.: WO2005/079867
PCT Pub. Date: Sep. 1, 2005

(65) Prior Publication Data
US 2008/0226547 A1 Sep. 18, 2008

Related U.S. Application Data

(60) Provisional application No. 60/546,878, filed on Feb. 23, 2004.

(30) Foreign Application Priority Data

Feb. 20, 2004 (GB) .................................... 0403856.8

(51) Int. Cl.
*A61K 51/02* (2006.01)
*A61K 51/12* (2006.01)
(52) U.S. Cl. ....................... 424/1.29; 424/1.49; 424/1.69
(58) Field of Classification Search .................. 424/1.11, 424/9.1, 9.3, 489, 499
See application file for complete search history.

(56) References Cited

U.S. PATENT DOCUMENTS

| | | | | |
|---|---|---|---|---|
| 4,970,062 | A | * | 11/1990 | Atcher et al. ................. 424/1.29 |
| 5,085,848 | A | | 2/1992 | Atcher et al. |
| 5,300,281 | A | * | 4/1994 | McMillan et al. ............ 424/1.29 |
| 5,609,850 | A | * | 3/1997 | Deutsch et al. ................ 424/9.5 |
| 6,592,843 | B2 | | 7/2003 | Larsen et al. |
| 6,635,234 | B1 | | 10/2003 | Larsen et al. |
| 6,740,304 | B2 | | 5/2004 | Larsen et al. |
| 7,056,275 | B2 | | 6/2006 | Larsen et al. |
| 2003/0206857 | A1 | | 11/2003 | Larsen et al. |
| 2004/0009955 | A1 | | 1/2004 | Larsen et al. |
| 2004/0184990 | A1 | | 9/2004 | Larsen et al. |
| 2004/0208821 | A1 | | 10/2004 | Larsen et al. |
| 2004/0258614 | A1 | * | 12/2004 | Line et al. .................... 424/1.11 |
| 2006/0135842 | A1 | | 6/2006 | Larsen et al. |
| 2006/0228297 | A1 | | 10/2006 | Larsen et al. |

FOREIGN PATENT DOCUMENTS

| | | |
|---|---|---|
| WO | WO 97/01304 | 1/1997 |
| WO | WO 01/28587 | 4/2001 |
| WO | WO 01/60417 | 8/2001 |

OTHER PUBLICATIONS

Michael R McDevitt et al. Radioimmunotherapy with alpha-emitting nuclides, European Journal of Nuclear Medicine, vol. 25(9), 1341-1351, 1998.*
The International Search Report for PCT/GB2005/000616, mailed Dec. 22, 2005.
Horwitz et al., "A lead-selective extraction chromatographic-resin and its application to the isolation of lead from geological samples," *Anal. Chim. Acta* 292(3):263-73 (1994).
Larsen et al., U.S. Appl. No. 11/665,197, filed Apr. 12, 2007.
Printout from http://www.eichrom.com/products/tech/pbresin.cfm (2 pages), copyright 2000.
Unni et al., "Preparation and bioevaluation of $^{166}$Ho labelled hydroxyapatite (HA) particles for radiosynovectomy," *Nucl. Med. Biol.* 29(2):199-209 (2002).
Vergote et al., "Therapeutic efficacy of the α-emitter $^{211}$At bound on microspheres compared with $^{90}$Y and $^{32}$P colloids in a murine intraperitoneal tumor model," *Gynecol. Oncol.* 47(3):366-72 (1992).

* cited by examiner

*Primary Examiner* — Michael G Hartley
*Assistant Examiner* — Jagadishwar Samala
(74) *Attorney, Agent, or Firm* — Clark & Elbing LLP

(57) ABSTRACT

The present invention provides Hydroxyapatite (HA) incorporating an alpha-emitting radionuclide or an in vivo generator for an alpha-emitting radionuclide. The invention further provides methods for the formation of such HA, pharmaceutical compositions comprising the HA and methods of medical treatment of cancerous or noncancerous disease including administering the HA or compositions thereof.

11 Claims, 1 Drawing Sheet

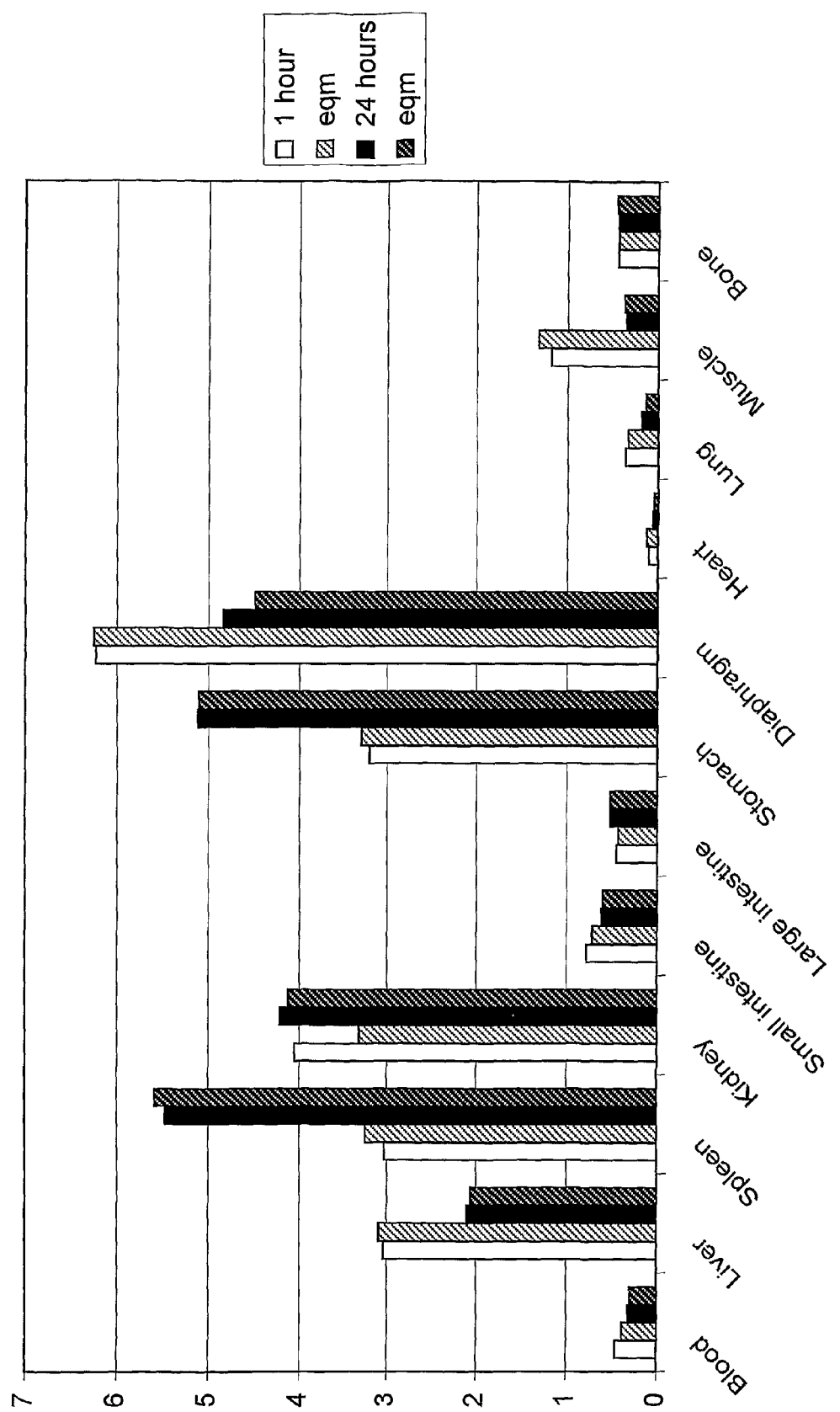

ALPHA-EMITTING HYDROXYAPATITE PARTICLES

CROSS REFERENCE TO RELATED APPLICATIONS

This application is the U.S. National Stage of International Application No. PCT/GB2005/000616, filed Feb. 18, 2005, which claims the benefit of U.S. Provisional Application No. 60/546,878, filed Feb. 23, 2004 and Great Britain Application No. GB 0403856.8, filed Feb. 20, 2004.

The present invention relates to a compositions suitable for delivering a radionuclide in vivo. In particular, the invention relates to particulate compositions comprising alpha-emitting radionuclides or generators for alpha-emitting radionuclides. The compositions of the invention are suitable for use in the treatment of both cancer and non-cancerous diseases.

The introduction of novel therapies is important in pharmaceutical research in all fields and particularly in cancer research. One field of this research relates to the use of radionuclides for therapeutic purposes. For many years, beta-particle emitters have been investigated for use in the treatment of cancers and colloids labeled with beta-particle emitters have been proposed to treat intracavitary disease including metastatic ovarian cancer.

In the recent years, efforts have also been made to utilize alpha-emitters in anti-tumor agents. Alpha-emitters have several features distinguishing them from beta-emitters including higher energies and shorter ranges in tissues. The radiation range of typical alpha emitters in physiological surroundings is generally less than 100 micrometers, the equivalent of only a few cell diameters. This makes these sources well suited for treatment of tumors including micrometastases because little of the radiated energy will pass beyond the target cells, and thus damage to the surrounding healthy tissue can be minimised. In contrast, a beta particle has a range of 1 mm or more in water.

The energy of alpha-particle radiation is also high compared to beta particles, gamma rays and X-rays, typically being 5-8 MeV, or 5 to 10 times that of a beta particle and 20 or more times the energy of a gamma ray. Thus, this deposition of a large amount of energy over a very short distance gives alpha radiation an exceptionally high linear energy transfer (LET), when compared to gamma or beta radiation. This explains the exceptional cytotoxicity of alpha-emitting radionuclides and also imposes stringent demands on the level of control and study of radionuclide distribution necessary in order to avoid unacceptable side effects.

It has been suggested that alpha-emitters be used bound to particulates and colloids for internal radionuclide therapy (see Bloomer et al., Int. J. Radiat. Oncol. Biol. Phys. 10 (3) 341-348 (1984); Rotmensch et al., Int. J. Radiat. Oncol. Biol. Phys. 34, 609-616 (1996); US 970062, U.S. Pat. No. 5,030,441, U.S. Pat. No. 5,085,848; and Vergote et al., Gynecol Oncol. 47(3):366-372 (1992) and Gynecol Oncol 47(3):358-65 (1992)).

One problem with these previously used particulate and colloidal carriers is that the carrier materials used are not biocompatible and biodegradable. As a result, the carriers may accumulate, particularly when administered repeatedly to a body cavity. This accumulation of non-biocompatible material may thus cause inflammation etc.

Another problem, particularly for instance with the prior art astatine-211 colloids and lead-212 colloids is leakage of free radionuclide, since astatine-211 and bismuth-212 (generated from lead-212) have been shown to accumulate in normal tissues like thyroid and stomach for astatine and the kidneys with bismuth.

A third problem with many of the radionuclides used, is that they are difficult to prepare and available only in small amounts or that they have a half-life so short that it renders them unsuitable for use in therapeutical preparations.

The very high energy of an alpha particle, combined with its significant mass, results in significant momentum being imparted to the emitted particle upon nuclear decay. As a result, an equal but opposite momentum is imparted to the remaining "daughter" nucleus in the form of a "nuclear recoil". This recoil is sufficiently powerful to break most chemical bonds and force the newly formed daughter nuclide out of chelation. This is highly significant where the daughter nucleus is itself alpha-radioactive because this daughter will no longer be confined by the particle or chelate complex in which the parent nucleus was administered. As a result, a significant problem with past methods for administering alpha-radiochemicals has been controlling the biodistribution of alpha-emitting daughter nuclides. This may limit the choice of alpha-emitters to those without alpha-emitting daughters or cause the dose to be limited so as to reduce the exposure of healthy tissue.

Where control over the biodistribution of daughter nuclei can be maintained then there is a considerable advantage in forming radiopharmaceuticals with alpha-emitters having a chain of further alpha-emitting daughters. By this method the dose received by healthy tissue during administration can be minimised and ideally several alpha decays can take place in the diseased area. If, however, control over the fate of daughter nuclei cannot be established then these become a problem if they are alpha-emitters. This is because they may then accumulate in healthy tissue and cause undesirable side-effects.

One method for maintaining control of alpha-emitting daughter nuclei was proposed in WO01/60417. This method employs chelation agent-containing liposomes to contain the alpha-emitters and prevent the nuclear recoil from propelling the daughter nuclei out into solution. Liposomes are, however, not ideal for all methods of administration and may show undesirable clearance rates and routes in some cases.

There is thus a considerable need for improved radiotherapeutic compositions showing stable labeling of alpha-emitting radionuclides and having little if any leakage of radioactive daughters to other tissues. There is further a need for radiotherapeutic compositions having biocompatible and biodegradable components. There is furthermore a need for radiotherapeutic compositions in which the radionuclides are sufficiently easy to prepare and available in sufficiently large amounts for use in pharmaceutical preparations.

The present inventors have now surprisingly established that hydroxyapatite (HA) particles may be radio-labelled with alpha emitting radionuclides and will stably retain the radionuclides over a considerable period. Furthermore, the present inventors have established that HA radio-labelled with alpha emitters will, to an unexpectedly high extent, retain daughter nuclides after decay of the parent nuclide. This was a highly unexpected finding since the recoil produced by the alpha decay usually disrupts chemical bonds and effects the release of the daughter product.

In a first aspect, the present invention therefore provides a hydroxyapatite (HA) incorporating an alpha-emitting radionuclide or a radionuclide which is an in vivo generator for an alpha-emitting radionuclide.

The hydroxyapatites of the present invention are preferably stable in the sense that the radionuclide is stably trapped within the HA and does not significantly leach out into solution or into other tissues under. physiological conditions. The HAs are furthermore preferably stable in the sense that the daughter nuclides are also trapped by the HA carrier and substantially do not leach out into solution or into other tissues under physiological conditions.

The hydroxyapatites of the invention and compositions prepared therefrom have the advantage of using the therapeutically stronger alpha-emitting radionuclides instead of the prior art beta-emitting nuclides while maintaining control over the daughter nuclei. Furthermore, desirable alpha-emitters which decay to provide a chain of further alpha-emissions may preferably be used because the hydroxyapatites of the present invention provide control over the fate of such daughters. The only known prior use of hydroxyapatite particulates as carriers has been for beta-emitting radionuclides in radiosynovectomy (i.e. in the treatment of pain from arthritis) by Unni et al. (Nucl Med Biol 29, 199-209 (2002)) and Brodack et al. (WO 97/01304). The beta-emitters used previously all decayed to stable nuclides of no relevance to the dose distribution (i.e. there was essentially no recoil upon decay and the daughter product was non-radioactive and therefore its distribution was not of any significance).

The hydroxyapatites of the present invention and the compositions prepared therefrom are highly suitable for use in the treatment of cancerous and non-cancerous diseases. This is especially because the therapeutically active alpha-emitters, administered directly with the hydroxyapatites of the invention or generated in vivo, provide high cytotoxicity and cause less damage to the deeper and surrounding regions of normal tissues as compared to beta-emitters. This applies particularly when the HAs of the invention are used in a local, regional or targeted administration method such as intracavitary, targeted systemic or intra-tumoural methods and results from the shorter range of alpha-radiation.

In a second aspect, the present invention therefore provides a method of treatment of a human or animal subject, especially a mammal (especially one in need thereof) by administration of an effective amount of a hydroxyapatite (HA) incorporating an alpha-emitting radionuclide or a radionuclide which is an in vivo generator for an alpha-emitting radionuclide or by administration of a composition prepared from such a HA.

In a further aspect, the present invention provides a pharmaceutical composition comprising a hydroxyapatite of the present invention and at least one physiologically acceptable carrier.

In a yet further aspect the present invention provides a hydroxyapatite (HA) incorporating an alpha-emitting radionuclide or a radionuclide which is an in vivo generator for an alpha-emitting radionuclide for use in therapy. In a still further aspect the invention provides the use of hydroxyapatite (HA) incorporating an alpha-emitting radionuclide or a radionuclide which is an in vivo generator for an alpha-emitting radionuclide in the manufacture of a medicament (especially an injectable, infusable or locally applicable medicament) for the treatment of a cancerous or non-cancerous disease (such as any of those diseases indicated herein below).

In a yet still further aspect, the invention relates to pharmaceutical compositions and devices comprising a hydroxyapatite (HA) incorporating an alpha-emitting radionuclide or an in vivo generator of an alpha-emitting radionuclide such as syringes pre-loaded with pharmaceutical preparations.

The invention further relates to a process for preparing a hydroxyapatite (HA) incorporating an alpha-emitting radionuclide or an in vivo generator of an alpha-emitting radionuclide, comprising the steps of:

(a) contacting a solution of an alpha-emitting radionuclide or an in vivo generator of an alpha-emitting radionuclide with hydroxyapatite particulates; and (b) optionally crystallizing a coating of hydroxyapatite on the labeled particulates prepared in step (a) whereby to encapsulate said radionuclide or said in vivo generator in the particulate.

Preferably, said process comprises:

(a) absorbing a solution of the alpha-emitter radionuclide or the in vivo generator of the alpha-emitter radionuclide to the hydroxyapatite particulates, preferably at a pH in the range of about 3-12; and (b) optionally crystallizing a coating of hydroxyapatite on the labeled particulates prepared in step (a)whereby to encapsulate said radionuclide in the particulate.

The term hydroxyapatite is used in the art to indicate a variety of related phosphated compounds, especially calcium hydroxyapatite which has the formula $[Ca_{10}(PO_4)_6(OH)_2]$. Calcium hydroxyapatite is a constituent of healthy bone matrix in all vertebrates. It is presently used as a material in artificial limbs, particularly in "cementless" bone inserts. A further use for hydroxyapatite is as selective cation exchangers in columns. Hydroxyapatite is a biocompatible and biodegradable material and it is therefore especially useful for in vivo application. In this connection, a further advantage is that it can be treated thermally or autoclaved. The present invention thus additionally provides products and compositions which are stable to autoclavation under standard conditions.

As used herein in the description and claims, the term hydroxyapatite (HA) is used to indicate any hydroxyapatite and any derivative or analogue thereof that is biocompatible or biodegradable. These should preferably not exhibit adverse effects for the intended use.

For example, the term hydroxyapatite or HA, as used herein encompasses calcium hydroxyapatite as well as any compound where the calcium ion, $Ca^{2+}$ is replaced by any other (preferably biotolerable) cation such as $Sr^{2+}$, $Ba^{2+}$, $Bi^{3+}$ or $Ac^{3+}$, or a combination of one or more of these cations. In one embodiment, hydroxyapatite comprising calcium hydroxyapatite is preferred. The HA may further be co-sedimented or crystallized with other minerals having low solubility, especially low solubility Ca-salts.

The HA useable in the present invention and referred to as hydroxyapatite or HA herein may further be surface modified to carry other substituents or groups, such as fluorine, phosphonates including bisphosphonates and tetraphosphonates, proteins, amino acids, peptides and magnetic substances.

Through surface modification, different properties, such as for instance a higher resistance to degradation, may be imparted to the particulate HA. Another use of surface modification is to include receptor binding molecules which can act as a targeting ligand to target biological target structures, especially tumour associated receptors.

Hydroxyapatite or HA as used herein also encompasses composites such as any hydroxyapatite compound combined or co-sedimented with other materials such as metals, oxides, proteins, amino acids, carbohydrates, phosphonates including bisphosphonates, organic compounds, e.g., polylactide, polyethyleneketones, glass-ceramics, titania, alumina, zirconia, silica, polyethylene, epoxy, polyethyleneglycol, polyhydroxybutyrate, gelatin, collagen, chitosan, phosphazene, iron, iron oxides and/or magnetic iron. Such combinations are useful for giving the final HA-particulates additional desirable properties, such as for instance magnetism (magnetic iron) or the ability to gel (gelatin, collagen, chitosan). Further, some of the groups mentioned above will render the HA more lipophilic, as is well know for a person skilled in the art, and this is considered an advantageous property for any HA derivative or analogue to be used in the present invention.

The hydroxyapatites that are suitable for use in the present invention can have any solid form, and will generally be called "particulates" in the present description and claims to distinguish them from the radio particles such as alpha particles (helium nuclei) or beta particles (electrons). The HA particulates can for instance be crystals, microspheres or colloids. The shape, size porosity and density of the particulates may be chosen to accommodate the intended use.

The size of the HA particulates may generally be in the range of from about 10 nm to about 100 μm, but colloids and other small particulates may be used including particulates as small as 1 nm.

In one embodiment, it is preferable that the particulates are of a size that they can remain in suspension without sedimentation. Sedimentation in this context being taken to include floatation, where the 'sediment' forms at the top, rather than the bottom of the suspension. In particular, it is preferable that the particulates are of a size such that they will not sediment when stored for a period of at least 1 hour, preferably at least 6 hours and most preferably at least 1 month when suspended in a fluid such as a pharmaceutically tolerable (especially aqueous) solution. Suitable particulate sizes will thus be readily determinable for any particular HA type by routine sedimentation experiments.

One especially preferred general size range for the HA particulates according to this invention will be from 1 μm to 20 μm, particularly from 1 μm to 5 μm.

It is preferable to use particulates having a substantially uniform size distribution. Different size ranges will be preferred and chosen depending on the intended use.

Small size particulates may distribute better in areas where there is a steric hindrance. Likewise, they may have advantages when the composition of the invention is administered intravenously (e.g. for cancer treatment systemically) or for delivery locally (e.g. to a cancer infected organ such as for instance the liver). Thus, one preferred small size range, particularly for intravenous administration, is about 1 nm to about 2 μm and a more preferred range is from about 8 nm to 40 nm.

In one embodiment, very small particulates are administered in order to preferentially target tumour cells. In particular, tumour capillaries may be more prone to leakage than capillaries in healthy tissue (e.g. due to their fenestration). Very small "nano-particulate" HA particulates of the present invention, (such as 1 to 50 nm, preferably 2 to 10 nm, more preferably 3 to 5 nm), may thus leak selectively from capillaries within tumours and so effectively target their incorporated radionuclides to the tumour site. Such particulates may also be attached to targeting moieties (such as antibodies or receptor binding molecules—see above) so as to increase this targeting effect.

On the other hand, larger size particulates may be better retained within the administered site e.g. in a body cavity. A second advantage of such larger particulates is that they are not as easily engulfed or broken down by macrophages and are thus expected to retain the radionuclide better in vivo.

Thus, a further preferred size range, particularly for administration to a body cavity, is about 100 nm to 100 μm and a more preferred range is from about 500 nm to 20 μm.

As used herein, the "size" of a particulate refers to the average (mode) size of the largest dimension of the particulates. The particulates may have any shape or mixture of shapes including spheres, plates, needles rods etc. but in general the longest dimension will be no more than 20 times, preferably no more than five times the shortest dimension. Where particulates are formulated for (especially intravenous or intra-arterial) injection or infusion it will generally be the case that no detectable proportion of particulates have any dimension greater than 8 μm, preferably 5 μm. Local or regional infection, e.g. to a cavity, intra-tumorally, subcutaneously or intramuscularly may not require this restriction.

Porosity is a second property of the HA particulates that may be chosen to correspond with the intended use or with the radionuclide to be labelled on the particulate. In particular, the porosity will be closely related to the density of the particulate and it will for some of the applications be favourable to choose HA particulates having a porosity that gives a density similar to water in order to achieve a very slow, if any, sedimentation.

Any radionuclide suitable for labelling HA to provide a composition according to the invention may be used in the present invention. This will be an isotope having or generating (e.g. by at least one beta decay) at least one alpha-radioactive nuclei. By the term an in vivo generator for an alpha-emitting radionuclide is meant a "parent" radionuclide which itself decays and in doing so provides a radioactive daughter nuclide, so providing a radioactive decay chain, wherein at least one of the nuclei in the chain decays by alpha-emission. Generally the parent nuclide will decay by beta emission. Also, the nuclei in the decay chain will typically have half-lifes such that a therapeutically significant amount of alpha-radiation is generated during the residence of the various nuclei within the body.

Where an isotope formulated in a composition of the invention is an alpha-emitter, it will preferably have a half-life of between 1 hour and 1 year, more preferably between 5 hours and 90 days One group of preferred nuclei includes the alpha emitting nuclei of the following group: $^{211}$At, $^{212}$Bi, $^{223}$Ra, $^{224}$Ra, $^{225}$AC, $^{227}$Th, and any combination thereof.

Another group of radionuclides are beta-emitters having at least one alpha-emitting daughter in their decay chain. These include, for example, $^{211}$Pb, which acts as a source for alpha-emitting $^{211}$Bi; $^{213}$Bi, which decays to alpha-emitting 213Po; and $^{225}$Ra, which beta-decays to provide $^{225}$Ac, and subsequently decays via four alpha and two beta emissions to finally yield stable $^{209}$Bi. One especially preferred example is: $^{212}$Pb, which decays via its alpha-emitting daughter $^{212}$Bi.

In one preferred embodiment of the invention, $^{212}$Pb/$^{212}$Bi suitable for use in the HA of the present invention may be prepared by a method comprising;
i) Preparing $^{224}$Ra (e.g. from a $^{228}$Thorium source by anion exchange chromatography),
ii) Purifying the $^{224}$Ra by contact with an f-block specific binder (e.g. an actinide/lanthanide-specific resin, especially in the form of a column),
iii) Allowing ingrowth of $^{212}$Pb (e.g. by allowing $^{224}$Ra to stand for 6-24 hours), and
iv) Purifying the resulting $^{212}$Pb by contact with a lead-specific binder (e.g. a Pb-specific resin, especially in the form of a column).

In the above method, any of the purification steps i), ii) and/or iv) may be repeated at least once with the same or different samples of specific binder. Suitable f-block element specific binders include methane bis-phosphonic acid derivatives such as P, P' di-octyl methane bis-phosphonic acid (e.g. DIPEX (RTM)). Suitable Pb specific binders include crown ethers, particularly 18-crown-6 derivatives such as di-t-butyl-cyclohexano-18-crown-6 (e.g. the Pb-B25-S cartridge containing Eichrom Pb specific resin). Where radionuclides are used, it is preferable to use specific binders on non-labile support such as silica but for purification where, contact with the resin is brief, organic resin supports may be used. This method may be combined with any method for forming HA incorporating radionuclides referred to herein. The $^{212}$Pb, and HA incorporating $^{212}$Pb formed and formable by these methods form further aspects of the invention.

The preparation method for $^{212}$Pb indicated above has the advantage of offering a simple and easily carried out procedure and also for providing $^{212}$Pb of greater radionuclide purity than has previously been obtainable.

The compositions of the present invention are stable to the loss of the loaded radionuclide from the HA particulates. A composition may be considered stable if, upon incubation in a solution at 37° C. for at least 20 minutes, at least 80% of the activity from the loaded radionuclide is detectable in the HA particulates rather than in the solution. This proportion should preferably be at least 85%, more preferably at least 90% and most preferably 95% or more.

The compositions are also stable to the loss of daughter nuclides generated from the decay (e.g. alpha decay) of the loaded radionuclide or one of its decay products. A composition may be considered stable in this respect if, upon incubation for a suitable period, the activity attributable to the daughter radionuclide generated during that period is distributed such that at least 70% remains associated with the HA particulates. This proportion is preferably at least 75%, more preferably at least 80% and most preferably at least 90%.

The labeling of hydroxyapatite with a radionuclide can for instance be performed through the following process steps of:

(a) absorbing a solution of the alpha-emitting radionuclide or the in vivo generator of the alpha-emitting radionuclide to the hydroxyapatite particulates, preferably at a pH in the range of about 3-12, more preferably at pH 5 to 10; and (b) optionally crystallizing a coating of hydroxyapatite on the labeled particulates prepared in step (a) to encapsulate said radionuclide in the HA particulate.

The method also preferably comprises the step of:

(c) heating the HA particles from step (a) or step (b) to a temperature of 70 to 150° C., preferably 80 to 130° C., more preferably 100 to 120° C.

The HA-particulates labeled according to (a) or (b) can be added to a biocompatible or physiologically acceptable liquid carrier (preferably an aqueous carrier) to prepare an injectable or infusable suspension or dispersion, together with any necessary or desirable excipient and/or additive. Additives include adjuvants suitable for preparing and stabilising a physiologically acceptable preparation for use in the treatment of cancer and in radiosynovectomy. Typically these additional components, where present, will be added before optional step (c).

Pharmaceutically tolerable carriers and excipients are well-known to a person skilled in the art and may include, for example, salts, sugars and other tonicity adjusters, buffers, acids, bases and other pH adjusters, viscosity modifiers, colourants, etc.

Alternatively HA-particulates labeled according to (a), followed by optional steps (b) and/or (c) can be included in a pharmaceutical gel composition, together with any necessary or desirable excipient and/or additives. Suitable additives will be well-known to persons skilled in the art and may include those indicated above and well known gelling agents such as natural and/or synthetic polymer gels. Compositions in gel form preferably have sustained release properties.

All other suitable pharmaceutical formulations that may be prepared starting from the HA particulates labeled with an alpha-emitting radionuclide or an in vivo generator for an alpha-emitting radionuclide, including liquids for injection or infusion, gels, creams, pastes, drops, patches, wipes, sprays, impregnated membranes and sheets etc, form further embodiments of the invention.

The most preferred pharmaceutical preparations of the compositions according to the invention are generally liquid, physiologically acceptable, injectable or infusable suspensions or dispersions. To prepare such pharmaceutical compositions the compositions of the invention are added to physiologically acceptable liquid carriers. Especially preferred are isotonic saline or phosphate buffers, but any other liquid carrier or carrier mixture that is physiologically acceptable and compatible with the inventive compound can be used. Many such liquid carriers or carrier systems are known by persons skilled in the art of preparing pharmaceutical preparations for in vivo injection and/or infusion.

The compositions of the present invention offer a further advantage in that they and/or the pharmaceutical preparations made therefrom may be heat-treated, for example, for the purposes of sterilisation. The compositions of the invention will typically be stable to heat treatment to above 70° C., preferably above 80° C. and more preferably to at least 100° C. This is particularly significant for larger particulates which will not easily be sterilised by filtration.

In order to avoid aggregation of the HA-particulates when in suspension, suitable modifiers or adjuvants as are well-known in the art, such as dispersion agents, may be added to the liquid pharmaceutical preparation according to the invention. Examples of such modifiers may be carbohydrates or proteins.

The effective dosage to be administered to a patient in need of treatment will be dependent on several factors such as the half life and decay chain of the radionuclide included in the composition according to the invention; the route of administration; the medical condition of the patient and his/her age and weight; as well as the illness to be treated. Such an effective dosage can be achieved through administration of a pharmaceutical composition according to the invention as one single dosage once; or through at least one single dosage per day (typically one, two or three per day) for a treatment period of at least one individual day or at least one day per week for one or more weeks or months. The treatment may be repeated at least once as deemed necessary or suitable by the skilled medical practitioner.

If a radionuclide having a short half life is used, it generally gives rise to a higher activity dosage per single administration as compared to a radionuclide having a longer half life.

Typical dosages will generally lie in the range from 10 kiloBq to 10 gigaBq per each single administration, with a more preferred range being 1 megaBq to 1 gigaBq per each single administration.

The compositions according to the present invention are useful in pharmaceutical compositions, especially preparations or devices in a liquid or gelled state and for the treatment of cancer and non-cancerous diseases.

As indicated above, the present invention provides, in various aspects, a method for treatment of cancer or non-cancerous diseases, compositions for use in such methods and the use of a composition for the manufacture of a medicament for use in such a treatment method. Diseases particularly applicable to these aspects of the invention include metastatic and non-metastatic cancerous diseases such as small cell and non-small cell lung cancer, malignant melanoma, ovarian cancer, breast cancer, bone cancer, colon cancer, bladder cancer, cervical cancer, sarcomas, lymphomas, leukaemias and tumours of the prostate. Other diseases particularly applicable to the application of these aspects of the invention include non-cancerous, especially hyperplastic diseases and for the reduction of pain in diseases (especially diseases of the bone) including arthritis.

Thus, one embodiment of these aspects relates to a method for treatment of a tumour locally. Such treatment may preferably be applied through an intratumoral injection or infusion to a subject (generally a human patient) in need of such treatment, of a therapeutically effective amount of a composition according to the invention. Such a method provides local irradiation of the tumor tissue. Alpha emitting radionuclides are highly effective in this embodiment because their range is short and damage to surrounding healthy tissue is minimised. Examples of diseases which may benefit particularly from this embodiment of the invention are those causing solid tumours, such as non-small cell lung cancer, malignant melanoma, ovarian cancer, colon cancer, sarcomas, and tumours of the prostate.

A further embodiment of the invention relates to methods for the treatment of locally disseminated cancers, such as for instance liver tumors, or peritoneally or intracranially confined diseases. This treatment may especially preferably be applied through loco-regional injections or infusions, to a subject in need of such treatment, of a therapeutically effective amount of a composition according to the invention.

Still another embodiment of the invention is a method for treatment of locally disseminated cancers such as liver tumors, through administration of a therapeutically effective amount of a liquid preparation comprising a radiolabeled HA according to the invention to a subject in need of such treatment, especially to said subject's blood supply to the affected area or organ, e.g. to the blood supply to the liver in the case of a liver tumor. This may promote transport of the composition into the tumor.

A further embodiment of the invention relates to a method for the treatment of systemically disseminated cancer by intravenous injection or infusion, or other systemic administration, to a subject in need of such treatment, of a therapeutically effective amount of a pharmaceutical preparation comprising a radiolabeled HA according to the invention.

A further embodiment of the invention relates to a method for treatment of intracavitary tumors, where a therapeutically effective amount of a radionuclide in the form of a composition of the present invention is administered to a subject in need of such treatment by injection or infusion into the tumor affected cavity and retained there in order to obtain irradiation of the cavity surfaces. Such cavities include the cranial cavity, peritoneal cavity and cavities created by pericardial effusion and mesothelioma and administration is suitable for cancers such as intracranial cancers, intraperitoneal cancers or cancers located in the cavities created by pericardial effusion and mesothelioma.

A further embodiment of the invention relates to a method for combination therapy, which comprises administration to a subject in need of such treatment of a therapeutically effective amount of the active radiolabeled HA according to the present invention and one or more additional treatments chosen from the group consisting of: surgery, chemotherapy and radiotherapy (especially external beam radiotherapy).

Combination therapy is a particularly preferred embodiment of the present invention and may be executed in a simultaneous, sequential or alternating manner, or any combination thereof. Thus, a combination treatment may comprise one type of treatment followed by one or more other types of treatment, wherein each type of treatment may be repeated one or more times. One example of simultaneous combination therapy is chemotherapy combined with the administration of a composition according to the present invention at the same point in time (either by the same or by a different method of administration). Such combination treatment may be combined with sequential therapy by starting simultaneous treatment, for instance, after a tumor has been removed surgically. The combination therapy may be repeated one or more times as needed based on the patient's condition.

An example of alternating combination therapy could be chemotherapy in one or more treatment periods alternating on different days or weeks with the administration of the pharmaceutical composition of the invention; or for instance surgery followed by one or more periods of treatment with the radiolabeled HA according to the invention.

A highly preferred embodiment of the invention relates to a method for treatment through applying a composition or device according to the invention in a therapeutically effective amount during surgery, after a procedure has been performed to remove cancerous material in a subject. The composition of the present invention may be applied at the tumor bed or to surrounding tissue. Such an application may be executed to achieve a sterilizing effect on the location of or surrounding the tumor bed and if applicable the cavity. This may be particularly useful in the event that tumor rupture occurs (e.g. during the surgical procedure). Such treatment may further also or alternatively achieve an anti-tumor effect on any remaining tumor cells at this location and/or in its proximity. This embodiment could be accomplished by using a suspension of the active compound (e.g. formulated as a spray or wipe). Alternatively, when relating to this method of treatment, it may be preferred that the composition of the invention is in the form of a paste, patch, impregnated sheet (especially an absorbable patch or sheet), cream or gel and especially a formulation (e.g. gel) providing a sustained release of the therapeutical radioactive agent.

Still another embodiment of the present invention relates to a method for synovectomy, i.e. to treat a subject suffering from pain in the joints and/or bones such as for instance pain arising from arthritis.

As used herein, the term "subject" will generally indicate a human patient but may also indicate a non-human mammalian subject, especially a canine or feline mammalian subject.

In the following section the invention is exemplified to show how the hydroxyapatite particulates may be labeled with an alpha-emitting radionuclide and a beta-emitting radionuclide, respectively. The examples are not to be considered limiting upon the invention. The invention is also illustrated by the attached FIGURE in which:

FIG. 1 shows the retention of $^{212}$Bi in various tissues after 1 and 24 hours following $^{212}$Pb administration. The Equilibrium level is also shown and demonstrates that the $^{212}$Bi levels are close to equilibrium.

GENERAL MATERIALS AND METHODS

Hydroxyapatite particulates used were Hydroxyapatite, Buffered aqueous suspension, Type 1 (Sigma, St. Louis, Mo., USA) or Macro-Prep Ceramic Hydroxyapatite Type 1, 20 μm (Bio Rad Laboratories, Hercules, Calif., USA).

Counters and Detectors: Gamma spectroscopy was performed with an EG&G Ortec GEM15-P Germanium Detector. General radioactivity counting was performed with a multiwell NaI detector (Packard Crystal II, Packard Instrument Co., Downers Grove, Ill., USA).

Particulate labelling and purification: The reaction mixture was mixed strongly on a whirlmixer (MS1 Minishaker, IKA, Germany) for 1 min and then incubated on a shaker for 30 minutes before centrifugation three times (5 minutes, 9000 rpm, MiniSpin centrifuge, Eppendorf, Germany) and two times washing of the pellet with 1 ml of 0.1 M citrate solution.

EXAMPLE 1

Preparation of Particulates Labeled with Radium-223.

Radium-223 was prepared from a $^{227}Ac/^{227}Th$ source immobilized on a DIPEX-2 column by eluting the $^{223}Ra$ with 1 M HCl. To the HCl eluate was added 0.1 M Na citrate until pH was above 5. To a 2 ml Eppendorfer tube were added 250 μl hydroxyapatite dispersion of 40 mg/ml and 50 μl of the $^{223}Ra$/citrate solution. And the labeling and purification performed as described in Materials and Methods section. The pellet bound activity was in excess of 96% for all three of the triplicate experiments carried out in parallel.

EXAMPLE 2

In vitro Stability Testing of $^{223}Ra$ Labeled HA-particulates.

The $^{223}Ra$-HA particulates described in Example 1 were added 500 μl of either 0.1 M sodium citrate or bovine serum albumin. The dispersion was incubated overnight at 37° C. and the solutions centrifuged according to Example 1. The pellet bound activity was in excess of 96% as measured after 20 minutes. A re-measurement performed two hours after showed no significant differences in count rates indicating that the distribution of daughter nuclides agreed well with those of the $^{223}Ra$.

In a further experiment, using ceramic HA particulates, $^{223}Ra$ (1 MBq) incorporated into 10 mg ceramic HA was incubated in foetal calf serum for two weeks at room temperature, after which 93.2% was pellet bound.

EXAMPLE 3

Preparation of $^{212}Pb$ and $^{212}Bi$ Labeled HA-particulates.

Lead-212 was prepared substantially free from $^{228}Th$ and $^{224}Ra$.

With $^{228}Th$ evaporated to dryness as starting material 0.5 ml 8M $HNO_3$ was added and the solution transferred to a column containing pre-equilibrated anion exchanger (AG1-X8). Radium-224 and daughters were extracted in 3 ml 8M $HNO_3$. Subsequently, the $^{224}Ra$ extract was evaporated to dryness, dissolved in 0.5 ml 1M HCl and purified on a DIPEX column (AC-resin, Eichrom Inc, Darien, Ill., USA), by eluting $^{224}Ra$ in 700 microliters 1M HCl to obtain a product free from thorium-228.

The next day (after-ingrowth of $^{212}Pb$) the $^{224}Ra$ eluate was evaporated to dryness and thereafter dissolved in 0.5 ml 1 M $HNO_3$ and transferred to a column containing a Pb-Specific resin (PB-B25-S, Eichrom). Radium-224 was eluted with 2 ml 1M $HNO_3$ and 2 ml distilled $H_2O$. Lead-212 was extracted from the Pb-resin using 650 microliters 0.1M ammonium oxalate solution.

The final $^{212}Pb$ solution was combinable directly with hydroxyapatite and reacted as described for $^{223}Ra$ in Example 1.

EXAMPLE 4

Stability Testing of $^{212}Pb$ and $^{212}Bi$ Labeled HA-particulates.

Lead-212 labeled HA was incubated in foetal calf serum overnight and thereafter centrifuged as described above. The pellet and supernatant associated radioactivity was measured. It was found that in excess of 93% of both $^{212}Pb$ and $^{212}Bi$ was associated with the pellet. The pellet bound activity fraction appeared to be slightly higher with the ceramic particulates.

EXAMPLE 5

Biodistribution of $^{212}Pb$ Labeled HA.

$^{212}Pb$ labeled HA (20 μm, ceramic) was prepared as described above washed and centrifuged three times and dissolved in 0.01 M sodium citrate/citric acid in isotonic saline solution at pH 7.4. To 7 female balb C mice with bodyweights of 21-25g was intra-peritoneally administered 0.5 ml suspension containing 0.4 MBq $^{212}Pb$ bound to 1.0 mg of HA. The animals were sacrificed at 1 h (n=3) and 24 h (n=4) and dissected. Results: The biodistribution data (Table 1) shows that the activity was almost quantitatively found in the i.p. cavity and at the organs and tissues within this cavity indicating very little leakage out from the cavity. The distribution pattern associated with free $^{212}Bi$, i.e., a high kidney accumulation, was not detected to a significant degree.

TABLE 1

Tissue distribution at 1 hour and 24 hours after intra-peritoneal injection of $^{212}Pb$ labelled to ceramic hydroxyapatite particulates.

| Tissue | 1 hour | 24 hours |
|---|---|---|
| Blood | (0.46 ± 0.40)/0.39 ± 0.34 | (0.32 ± 0.19)/0.30 ± 0.24 |
| Liver | (3.04 ± 2.83)/3.09 ± 2.93 | (2.10 ± 1.56)/2.06 ± 1.45 |
| Spleen | (3.03 ± 1.11)/3.25 ± 1.21 | (5.47 ± 5.21)/5.58 ± 5.27 |
| Kidney | (4.05 ± 3.08)/3.32 ± 2.84 | (4.21 ± 3.29)/4.12 ± 3.39 |
| Small intestine | (0.78 ± 0.86)/0.72 ± 0.80 | (0.62 ± 0.25)/0.60 ± 0.26 |
| Large intestine | (0.45 ± 0.41)/0.43 ± 0.38 | (0.52 ± 0.39)/0.52 ± 0.40 |
| Stomach | (3.20 ± 2.09)/3.29 ± 2.18 | (5.11 ± 2.79)/5.10 ± 2.79 |
| Diaphragm | (6.23 ± 2.39)/6.25 ± 2.33 | (4.84 ± 1.95)/4.49 ± 2.47 |
| Heart | (0.10 ± 0.11)/0.12 ± 0.13 | (0.06 ± 0.06)/0.04 ± 0.03 |
| Lung | (0.36 ± 0.29)/0.33 ± 0.27 | (0.18 ± 0.12)/0.13 ± 0.09 |
| Muscle | (1.18 ± 1.89)/1.32 ± 2.14 | (0.35 ± 0.58)/0.37 ± 0.67 |
| Bone | (0.44 ± 0.46)/0.44 ± 0.47 | (0.44 ± 0.20)/4.49 ± 2.47 |

Number in brackets: Tissues measured approximately 1 hour after sacrificing the animals. Numbers in bold print: tissues measured one day after sacrificing the animals, i.e. allowing time for daughter nuclides to be in equilibrium with the $^{212}Pb$ mother nuclide. If the number in the bracket is lower than the corresponding bold number it indicates a depletion of the $^{212}Bi$ daughter nuclide vs $^{212}Pb$ in the tissue at the time of death (the opposite would mean enrichment of $^{212}Bi$ vs $^{212}Pb$ at the time of death).

The invention claimed is:

1. A pharmaceutical composition comprising a hydroxyapatite (HA) incorporating a parent alpha-emitting radionuclide selected from the group consisting of $^{211}At$, $^{212}Bi$, $^{223}Ra$, $^{224}Ra$, $^{225}Ac$, and $^{227}Th$ or a parent beta-emitting radionuclides $^{212}Pb$, $^{211}Pb$, $^{213}Bi$, and $^{225}Ra$, wherein the HA retains at least 70% of the activity attributable to the daughter radionuclide after the decay of the patent radionuclide.

2. Hydroxyapatite according to claim 1, wherein the HA comprises a cation that is bivalent or trivalent or a mixture of such cations.

3. Hydroxyapatite according to claim 2 wherein the cation is chosen from the group consisting of calcium, strontium, barium, bismuth, yttrium, lanthanum, lead or mixtures thereof.

4. Hydroxyapatite according to claim 1, wherein the HA is particulate and has a size in the range of 1 nm to 100 μm.

5. Hydroxyapatite according to claim 4 wherein the HA has a size in the range of 1 μm to 20 μm.

6. Hydroxyapatite according to claim 1, wherein the HA is surface modified with amino acids, peptides, proteins, antibodies, carbohydrates, phosphonates, fluorine, magnetic substances, folate groups or a combination thereof.

7. Hydroxyapatite according to claim 1, wherein the HA is combined or co-sedimented with a substance selected from the following group: metals, oxides, proteins, amino acids, carbohydrates, phosphonates including bisphosphonates or organic compounds.

8. Hydroxyapatite according to claim 1, wherein the HA is combined or co-sedimented with a substance selected from polylactide, polyethyleneketones, glass-ceramics, titania, alumina, zirconia, silica, polyethylene, epoxy, polyethyleneglycol, polyhydroxybutyrate, gelatin, collagen, chitosan, phosphazene, iron, iron oxides, magnetic iron or mixtures thereof.

9. A pharmaceutical composition as claimed in claim 1, wherein the composition comprises a physiologically acceptable carrier.

10. A pharmaceutical composition according to claim 9 in liquid, injectable form.

11. A pharmaceutical composition according to claim 9 in gel form.

* * * * *

UNITED STATES PATENT AND TRADEMARK OFFICE
CERTIFICATE OF CORRECTION

PATENT NO.         : 8,142,758 B2  
APPLICATION NO.    : 10/588839  
DATED              : March 27, 2012  
INVENTOR(S)        : Roy H. Larsen et al.

Page 1 of 1

It is certified that error appears in the above-identified patent and that said Letters Patent is hereby corrected as shown below:

Title Page, Item (56) under OTHER PUBLICATIONS, replace "vol" with --Vol--.

Column 12, Claim 1, Line 48, replace "radionuclides $^{212}$Pb," with --radionuclide $^{212}$Pb--;

Claim 1, Line 48, replace "and $^{225}$Ra," with --or $^{225}$Ra,--; and

Claim 1, Line 50, replace "patent" with --parent--.

Signed and Sealed this  
Fifth Day of February, 2013

Teresa Stanek Rea  
*Acting Director of the United States Patent and Trademark Office*